US012734062B2

(12) United States Patent
Czaplewski et al.

(10) Patent No.: US 12,734,062 B2
(45) Date of Patent: Sep. 15, 2026

(54) OSTOMY FILTER

(71) Applicant: Hollister Incorporated, Libertyville, IL (US)

(72) Inventors: Gregory J. Czaplewski, Bloomingdale, IL (US); Kanav Kumar, Chicago, IL (US)

(73) Assignee: HOLLISTER INCORPORATED, Libertyville, IL (US)

( * ) Notice: Subject to any disclaimer, the term of this patent is extended or adjusted under 35 U.S.C. 154(b) by 559 days.

(21) Appl. No.: 18/549,451

(22) PCT Filed: Mar. 8, 2022

(86) PCT No.: PCT/US2022/019356
§ 371 (c)(1),
(2) Date: Sep. 7, 2023

(87) PCT Pub. No.: WO2022/197488
PCT Pub. Date: Sep. 22, 2022

(65) Prior Publication Data

US 2024/0173161 A1 May 30, 2024

Related U.S. Application Data

(60) Provisional application No. 63/162,928, filed on Mar. 18, 2021.

(51) Int. Cl.
*A61F 5/441* (2006.01)

(52) U.S. Cl.
CPC .................................... *A61F 5/441* (2013.01)

(58) Field of Classification Search
CPC ............... A61F 5/441; A61F 2005/4415–4495
See application file for complete search history.

(56) References Cited

U.S. PATENT DOCUMENTS 5,423,782 A * 6/1995 Wolrich .................. A61F 5/445
604/339
5,976,118 A 11/1999 Steer
(Continued)

FOREIGN PATENT DOCUMENTS

JP 2013526989 A 6/2013
WO WO2008136413 A1 11/2008
WO 2021186249 A1 9/2021

OTHER PUBLICATIONS

Japanese Search Report issued in connection with JP application No. 2023-556928 and machine translation thereof mailed dated Aug. 20, 2025, 5 pages.
(Continued)

*Primary Examiner* — Susan S Su
(74) *Attorney, Agent, or Firm* — Klintworth & Rozenblat LLP

(57) ABSTRACT

An ostomy pouch includes a body-side wall and a distal-side wall joined at an outer periphery and defining an interior volume comprising a collection area. The ostomy pouch also includes an inlet for receiving ostomy effluent, an outlet for egress of gas collected in the collection area, and a filter assembly covering the outlet. The ostomy pouch is configured to have an airflow rate @ 0.18 psi of greater than about 10 cc/s and less than about 40 cc/ss and a liquid (water) hold-out of greater than about 0.9 psi and less than about 6.0 psi.

13 Claims, 7 Drawing Sheets

(56) References Cited

U.S. PATENT DOCUMENTS

| | | | | |
|---|---|---|---|---|
| 2005/0143696 | A1* | 6/2005 | Pedersen | A61F 5/448 604/332 |
| 2006/0271002 | A1 | 11/2006 | Botten | |
| 2013/0072886 | A1* | 3/2013 | Schertiger | A61F 5/441 604/335 |
| 2014/0371698 | A1 | 12/2014 | Chang et al. | |

OTHER PUBLICATIONS

Japanese Office Action issued in connection with JP application No. 2023-556928 and machine translation thereof mailed dated Sep. 2, 2025, 5 pages.

International Search Report and Written Opinion for PCT/US2022/019356 mailed dated Jun. 22, 2022, 12 pages.

European Office Action issued in connection with EP application No. 22713801.3 dated Jun. 18, 2025, 04 pages.

* cited by examiner

OSTOMY FILTER

This is a National Stage Application of International Patent Application No. PCT/US2022/019356, filed Mar. 8, 2022, which claims the benefit of and priority to U.S. Provisional Application No. 63/162,928, filed Mar. 18, 2021, the entirety of which are incorporated fully herein by reference.

BACKGROUND

The following description relates to an ostomy appliance, and more particularly, a deodorizing filter for an ostomy appliance.

An ostomy bag or pouch includes an inlet configured to receive liquid, semisolid or solid bodily waste discharged from a stoma for collection within the pouch. A known pouch also includes a filter assembly to facilitate odor filtering and egress of gas from the pouch. However, in some instances, liquid, semisolid or solid contents (i.e., bodily waste) may flow to and block the filter assembly, thereby restricting egress of gas through the filter assembly. This may lead to ballooning of the pouch caused by a build-up of gas pressure and undesirable inflation of the pouch.

Disruption to quality of life from the pouch ballooning can be significant for ostomates, for example, anxiety, lack of discretion, fear of leakage, nighttime considerations, inconvenient user intervention to release gas pressure, etc. Some common methods to release built-up gas include opening a pouch coupling system, which is often referred to as "burping", draining a pouch, and peeling back a skin barrier. Many ostomates have reported spending many hours troubleshooting the pouch ballooning issues and feeling resigned about the current ostomy pouch systems.

Further, the cost of a filter assembly is relatively high, making up a substantial portion of the total cost for an ostomy appliance.

Accordingly, it is desirable to provide a cost-effective filter assembly for an ostomy appliance that can minimize ballooning.

SUMMARY

In one aspect, an ostomy pouch may be configured to have an airflow rate @ 0.18 psi of greater than about 10 cc/s and less than about 40 cc/s and a liquid (water) hold-out of greater than about 0.9 psi and less than about 6.0 psi. The ostomy pouch may include a body-side wall and a distal-side wall joined at an outer periphery and defining an interior volume comprising a collection area. The ostomy pouch may further comprise an inlet for receiving ostomy effluent, an outlet for egress of gas collected in the collection area, and a filter assembly arranged to cover the outlet. The filter assembly may comprise a backing layer, a filter media, and a membrane layer, wherein the backing layer has a lower gas permeability than the filter media.

In an embodiment, the membrane layer may be formed from a spunbond-meltblown-spunbond polypropylene (SMS PP) nonwoven. The filter media may be formed from an activated carbon impregnated foam, which may be hydrophobic. For example, the filter media may be formed from an activated carbon impregnated reticulated polyurethane (PU) foam. The pouch gas outlet may be defined by an opening having an area of about 0.06 $inch^2$ to about 0.07 $inch^2$.

In an embodiment, the backing layer may be formed from a low density polyethylene film, the filter media may be formed from an activated carbon reticulated PU foam having a net density of about 26 $kg/m^3$ to about 30 $kg/m^3$ (tested according to ISO 845), and the membrane layer may be formed from a SMS PP nonwoven having a basis weight of about 44 gsm. The pouch gas outlet may be defined by an opening having an area of about 0.06 $inch^2$ to about 0.07 $inch^2$. The ostomy pouch may be configured to have an airflow rate @0.18 psi of greater than about 10 cc/s and less than about 40 cc/s and a liquid (water) hold-out of greater than about 0.9 psi and less than about 3.0 psi.

In another embodiment, the backing layer may be formed from a low density polyethylene film, the filter media may be formed from an activated carbon reticulated PU foam having a net density of about 26 $kg/m^3$ to about 30 $kg/m^3$ (tested according to ISO 845), and the membrane layer may be formed from a SMS PP nonwoven having a basis weight of about 44 gsm. The pouch gas outlet may be defined by an opening having an area of about 0.0625 $inch^2$. The ostomy pouch may be configured to have an airflow rate @0.18 psi of greater than about 15 cc/s and less than about 35 cc/s and a liquid (water) hold-out of greater than about 1.0 psi and less than about 2.0 psi.

In an embodiment, the filter assembly may be attached to an outer surface of one of the body-side wall and the distal-side wall and configured to provide a radial gas flow path through the filter media. In such an embodiment, the filter assembly may be configured to allow the gas egressing through the outlet to flow through the membrane layer and radially flow through the filter media and exit the filter assembly through at least one gas outlet provided proximate an outer periphery of the filter assembly.

In some embodiments, the ostomy pouch may further comprise a prefilter and a protective panel, which may be configured to protect the filter assembly from ostomy effluent. The filter assembly may be attached to an outer surface of the distal-side wall and the prefilter and the protective panel may be attached to an inner surface of the distal-side wall. In such an embodiment, the ostomy pouch may be configured to provide a flow path for the gas collected in the collection area to flow through microperforations provided in the protective panel, and flow through the prefilter, and exit the ostomy pouch through the outlet, and flow through the membrane layer, and flow through the filter media radially before exiting the filter assembly.

In an embodiment, the filter assembly may be attached to an inner surface of one of the body-side wall and the distal-side wall and configured to provide a radial gas flow path through the filter media. In such an embodiment, the filter assembly may be configured to allow the gas collected in the collection area to flow into the filter assembly through at least one gas inlet provided proximate an outer periphery of the filter assembly, and radially flow through the filter media, and flow through the membrane layer before exiting the ostomy pouch through the outlet.

In some embodiments, the ostomy pouch may further comprise a prefilter and a protective panel, wherein the filter assembly, the prefilter and the protective panel may be attached to an inner surface of the distal-side wall. In such an embodiment, the ostomy pouch may be configured to provide a flow path for the gas collected in the collection area to flow through microperforations provided in the protective panel, and flow through the prefilter, and enter the filter assembly through at least one gas inlet provided proximate an outer periphery of the filter assembly, and radially flow through the filter media, and flow through the membrane layer before exiting the ostomy pouch through the outlet.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
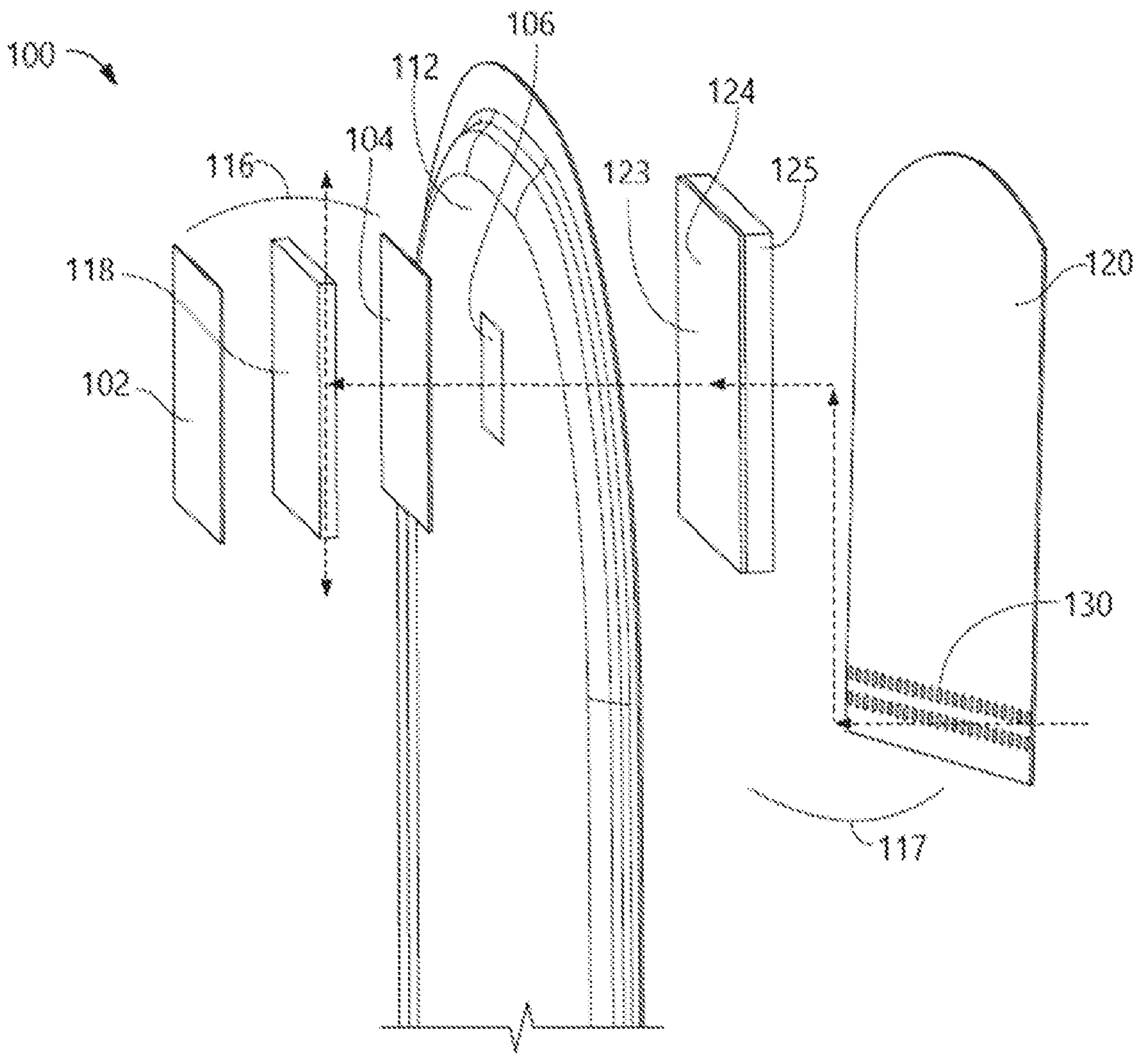
FIG. 1 is a partial exploded view of an ostomy pouch comprising a filter assembly according to an embodiment.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

FIG. 1 is a partial exploded view of an ostomy pouch 100 according to an embodiment. The ostomy pouch 100 may comprise a filter assembly 116. In some embodiments, the ostomy pouch 100 may also comprise a multi-stage protection 117 including a protective panel 120 and a prefilter 124. In the embodiment of FIG. 1, the filter assembly 116 may be attached to an outer surface of a pouch wall 112 while the multi-stage protection 117 may be arranged inside the pouch.

The filter assembly 116 may comprise a backing layer 102, a filter media 118, and a membrane layer 104. The filter assembly 116 may be arranged to cover a gas outlet opening 106 defined in the pouch wall 112 and attached to the pouch wall 112, for example via heat sealing. The membrane layer 104 may be formed from a suitable gas permeable material configured to allow gas to flow therethrough while providing protection against ostomy effluent. The filter media 118 may be formed from a suitable filter material configured to deodorize ostomy gas. The backing layer 102 may be formed from a suitable material that has a relatively low gas permeability or gas impermeable and configured to direct gas to flow radially through the filter assembly 116. In this embodiment, gas collected in the ostomy pouch 100 may egress through the outlet opening 106 and flow into the filter assembly 116 through the membrane layer 104 and radially flow through the filter media 118 before exiting the filter assembly 116 as indicated by arrows in FIG. 1. The filter assembly 116 may comprise at least one gas outlet proximate a periphery of the filter assembly 116. For example, the filter assembly 116 may comprise a gas outlet defined by an unsealed periphery.

The radial gas flow length through the filter media 118 may be determined by the size of the outlet opening 106 and the size of the filter media 118 (larger the outlet opening 106, shorter the gas path through the filter media 118). Further, the flow rate of gas egressing the ostomy pouch 100 through the filter assembly 116 may be adjusted by configuring the size of the outlet opening 106 and gas flow properties of the membrane layer 104, such as a porosity of the membrane layer 104. In an embodiment, the size of the outlet opening 106 and the membrane layer 104 may be configured to allow sufficient gas egress to minimize pouch ballooning while still providing a gas flow length through the filter media 118 for excellent odor deodorization.

In an embodiment, the outlet opening 106 may have an area of about 0.02 $inch^2$ to about 0.15 $inch^2$, preferably about 0.05 $inch^2$ to about 0.08 $inch^2$, and more preferably 0.06 $inch^2$ to about 0.07 $inch^2$. The outlet opening 106 may be provided in various shapes, for example, circular opening, elliptical opening, rectangular opening, square opening, etc. In an embodiment the outlet opening 106 may be defined by a square shaped opening having an area of about 0.0625 $inch^2$ (0.25 inches×0.25 inches).

Suitable materials for the backing layer 102 may include, but are not limited to, polymeric films having a substantially lower gas permeability compared to the filter media 118. For example, the backing layer 102 may be formed from a polymeric film, such as a low density polyethylene (LDPE) film. The backing layer 102 may have a thickness of about 2 mil to about 10 mil, preferably about 3 mil to about 7 mil, and more preferably about 5 mil.

Figure 2:
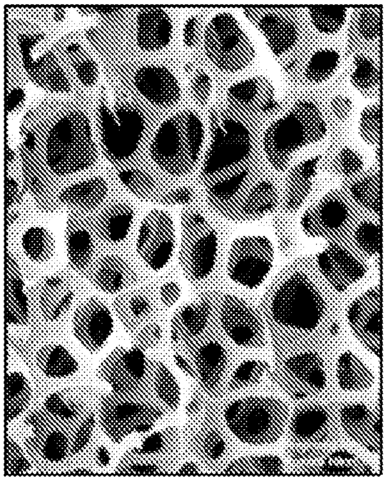
FIG. 2 is a microscopic image of a reticulated foam according to an embodiment.
Figure 3:
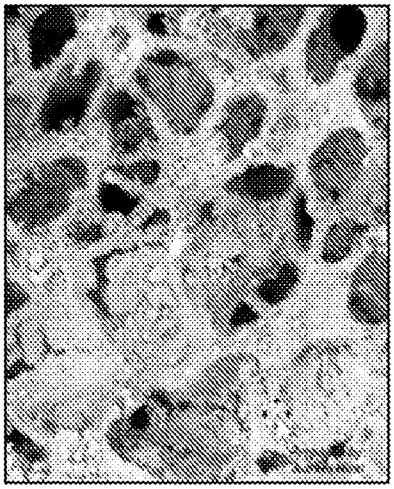
FIG. 3 is a microscopic image of a reticulated foam filled with activated carbon according to an embodiment.

The filter media 118 may be formed from a suitable filter material comprising charcoal, carbon or other suitable deodorizing materials for deodorizing gas. Suitable filter materials for the filter media 118 may include, but are not limited to, activated carbon foam materials, such as a filter material comprising a reticulated foam and activated carbon, activated carbon nonwoven, and activated carbon cloth. FIG. 2 is a microscopic image of a reticulated foam according to an embodiment, and FIG. 3 is a microscopic image of a reticulated foam filled with activated carbon according to an embodiment. The filter media 118 may have a thickness of about 0.03 inches to about 0.15 inches, preferably about 0.06 inches to about 0.12 inches, and more preferably about 0.07 inches to about 0.1 inches.

In an embodiment, the filter media 118 may be formed from a reticulated polyurethane (PU) foam comprising activated carbon and having a thickness of about 0.089 inches, such as PU foam filter materials available from Freudenberg. Such a PU foam filter material may be hydrophobic and may provide additional advantages for the filter assembly 116 arranged on an outer surface of the pouch. For example, the hydrophobic filter media 118 may resist water and eliminate a need for a filter sticker when the filter assembly 116 is exposed to water, for example during shower or swimming.

The membrane layer 104 may be formed from a suitable gas permeable material. Suitable gas permeable materials for the membrane layer 104 may include, but are not limited to, ePTFE (expanded polytetrafluoroethylene) membrane, UHMW PE (ultra high molecular weight polyethylene) membrane, pulp/polyester membrane, spunmelt PP (polypropylene) membrane, SMS PP (spunbond meltblown spunbond polypropylene) nonwoven, and the like. The membrane layer 104 may have a thickness of about 0.5 mil to about 15 mil, preferably about 0.8 mil to about 12 mil. In an embodiment, the membrane layer 104 may be formed from a tri-laminate SMS PP nonwoven comprising a spunbond PP top layer, a meltblown PP middle layer, and a spunbond PP bottom layer having a basis weight of about 10 $g/m^2$ (gsm) to about 500 gsm, preferably about 30 gsm to about 120 gsm, and more preferably about 40 gsm to about 80 gsm. For example, the membrane layer 104 may be formed from a SMS PP nonwoven having a basis weight of about 44 gsm available under Style T063-73960 from Precision Fabrics Group Inc. In another embodiment, the membrane layer 104 may be formed from a microporous UHMW PE membrane having a basis weight of about 1 gsm to about 20 gsm, preferably about 2 gsm to about 5 gsm, a thickness of about 10 μm to about 50 μm, preferably about 15 μm to about 40 μm, and a porosity of about 60% to about 90%, preferably about 70% to about 85%. For example, the membrane layer 104 may be formed from a microporous UHMW PE membrane having a basis weight of about 3 gsm, a thickness of about 20 μm, and a porosity of about 83%, which is available under the tradename Solupor® membranes 3P07A from Lydall Performance Materials B.V.

In an embodiment, the filter assembly 116 may be configured to minimize ballooning while still providing excellent odor filtration and preventing ostomy effluent leakage. Such properties of a filter assembly may be evaluated by analyzing airflow rate through the filter assembly, liquid hold-out, which measures a pressure at which a liquid is forced through a membrane layer of the filter assembly, and deodorization data.

In the embodiment of FIG. 1, the airflow rate and liquid hold-out of the filter assembly 116 may be mainly determined by the properties of the membrane layer 104. The cost of the membrane layer for many prior art filter assemblies, for example, those including a membrane layer formed from an ePTFE membrane or UHMW PE membrane, is often the largest portion of the total material cost of the filter assembly. For example, the cost of the membrane layer formed from an ePTFE membrane may make up over 50% of the total material cost of a filter assembly.

The inventors of the present application have researched and analyzed numerous different membrane materials, nonwoven materials, fabric materials, and other gas permeable materials to identify a suitable material for a filter membrane layer that can provide comparable or better filter properties at a substantial cost saving. After substantial time and investment in research and development, it was discovered that a filter assembly comprising a membrane layer formed from a SMS PP nonwoven material, which is typically used for hospital gowns, may provide surprisingly excellent filter membrane properties, such as airflow rate and liquid hold-out, at a substantially lower cost. For example, the cost of a SMS PP nonwoven material can be as low as about 1% of the cost of an ePTFE membrane material or a UHMW PE membrane material. Airflow rate and liquid hold-out data for various membrane materials are shown in Table 1.

TABLE 1

Airflow Rate and Liquid Hold-Out Data of Filter Membranes

| Membrane | Airflow rate @0.18 psi (cc/s) | Liquid ($H_2O$) hold-out (psi) |
|---|---|---|
| SMS PP nonwoven (T063-73960, PFG) | 28.6 (filter assembly) | 1.32 (membrane only) |
| Spunmelt PP | 22.4 (filter assembly) | 0.7 (membrane only) |
| Pulp/polyester | 20.9 (filter assembly) | 0.27 (filter assembly) |
| UHMW PE (Solupor ® 3P07A, Lydall) | 8.06 (membrane only) | 4 (membrane only) |
| e-PTFE | 11.2 (filter assembly) | 6 (filter assembly) |
| e-PTFE | 7.28 (filter assembly) | 6 (filter assembly) |
| UHMW PE | 4.1 (filter assembly) | >10 (filter assembly) |

The airflow rate was tested using Isaac HD Multi-Function Leak Tester (Isaac tester) equipped with a Mass Flow Meter (MFM), which measures a mass flow rate of air through a pouch to maintain a specified pressure. A square shaped and Teflon coated test plate including alignment holes near each of the corners and an opening in the center to allow air to pass into a pouch was used to mount a pouch. A test fixture including two air cylinders was used to clamp the test plate and the pouch mounted thereto. The test fixture included a hole defined therein to allow air to pass from a pressure transducer into the pouch.

Figure 4:
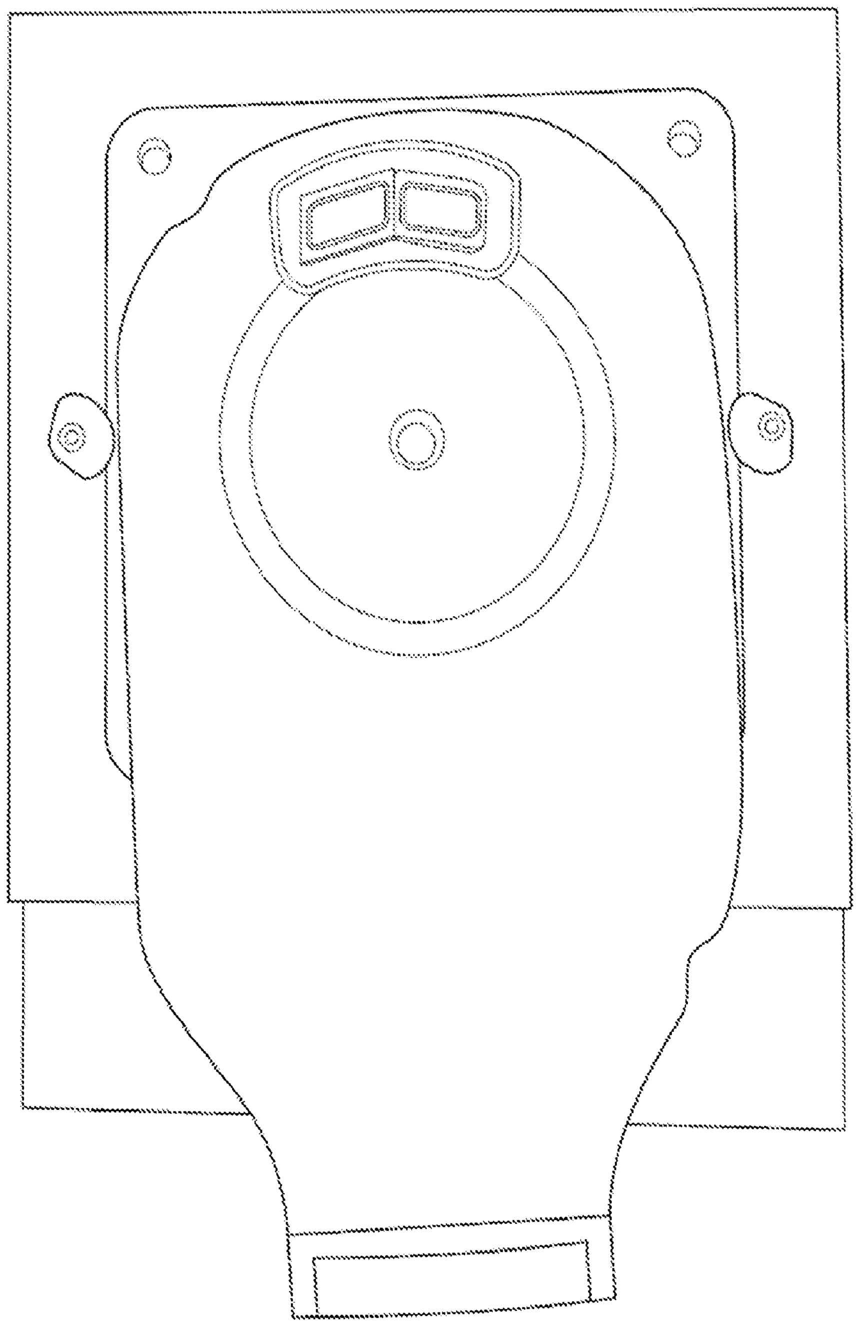
FIG. 4 is an illustration of an ostomy pouch mounted on a test fixture for an airflow rate test according to an embodiment.

The airflow rate data in Table 1 were collected by measuring an air flow rate to maintain a 0.18 psi pressure in a sample pouch including a filter assembly or a membrane (as indicated in Table 1) attached thereto to cover a gas outlet opening. The sample pouch was attached to the test plate by removing a barrier backing and centering a pouch starter hole over the center hole of the test plate, such that no air channels are formed between the barrier and the test plate. The test plate with the pouch mounted thereto is attached to the test fixture using the locating pins to guide alignment and pneumatically clamped as shown in FIG. 4. Using the Isaac tester, an air flow rate to maintain a pressure of 0.18±0.018 psi was measured and recorded.

Figure 5:
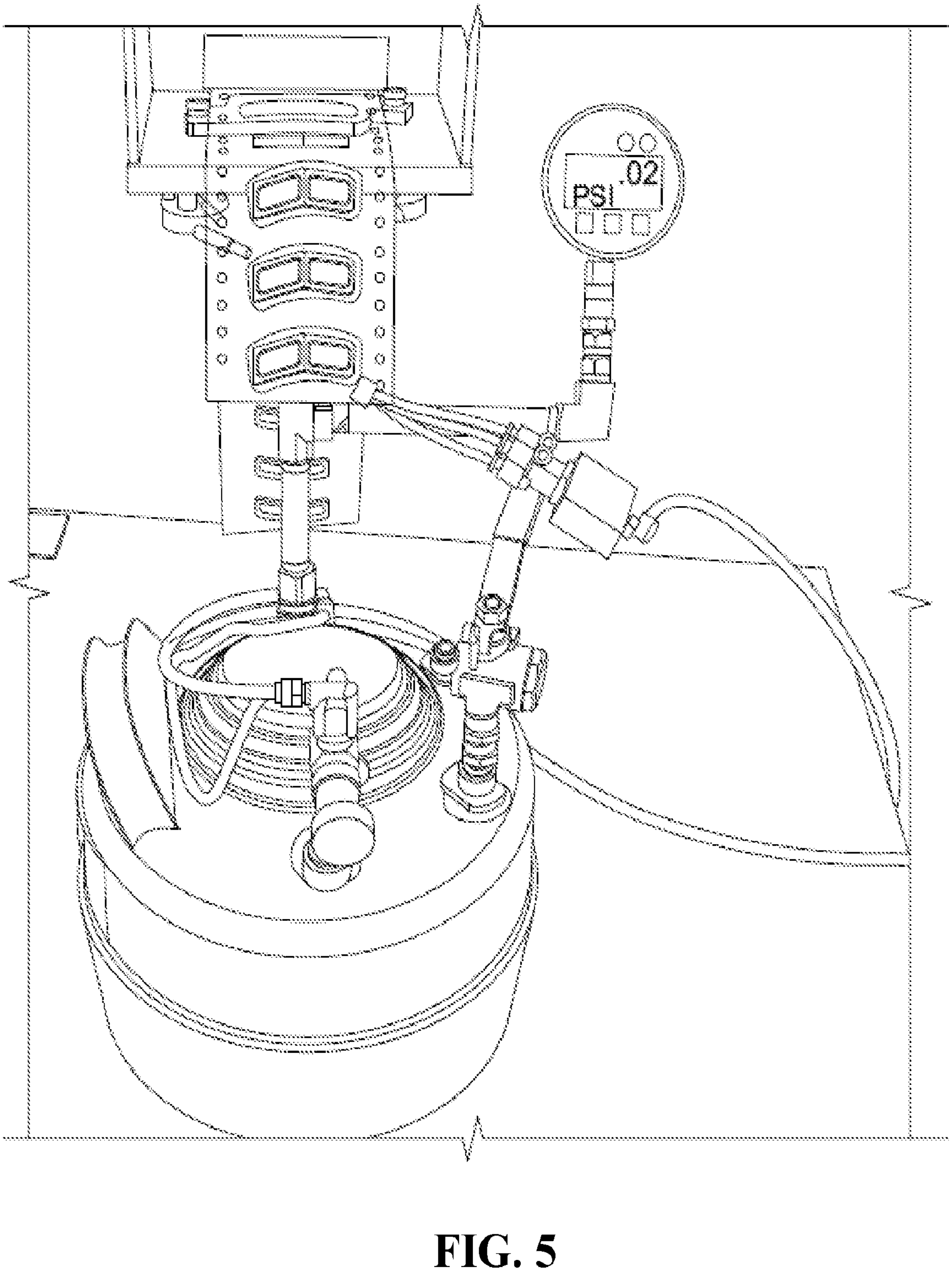
FIG. 5 is an illustration of a liquid hold-out test set up according to an embodiment.
Figure 6:
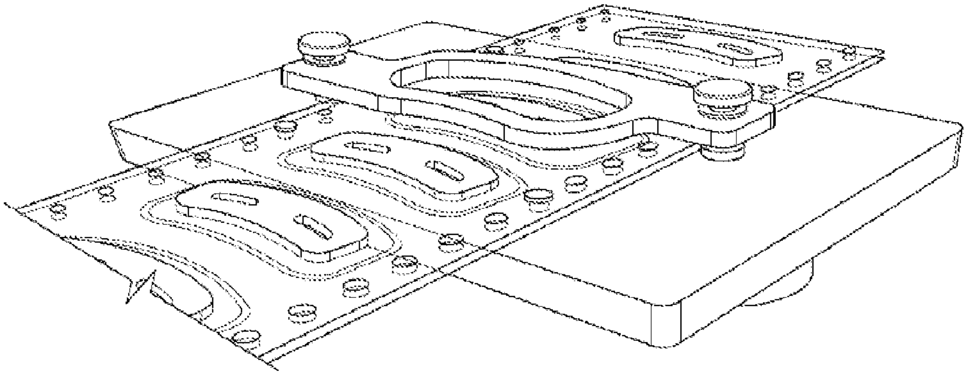
FIG. 6 is an illustration of an ostomy filter clamped in a test fixtured in the liquid hold-out test set up of FIG. 5.

The liquid hold-out was tested using a test equipment system including a liquid pressure tank, an air source, and a liquid pressure gauge (FIG. 5) to measure a pressure at which a liquid (water was used for the data provided in Table 1) is forced through a membrane or a membrane layer of a filter assembly. A sample membrane or a sample filter assembly (as indicated in Table 1) was placed on a fixture and a filter clamp was positioned over the fixture, such that the filter clamp is aligned over the membrane or filter assembly as shown in FIG. 6. After closing the filter clamp via a pneumatic valve, the system pressure was raised until water penetrated the sample membrane or the membrane layer of the sample filter assembly.

After detailed examination and careful studies of ostomy pouch ballooning phenomenon, effluent leakage through ostomy filters, and filtering of ostomy gas, and analyses of airflow rate and liquid hold-out data of numerous membrane materials and filter assemblies, it was discovered that an ostomy pouch comprising a filter assembly configured to have an airflow rate @ 0.18 psi of greater than about 10 cc/s and less than about 40 cc/ss and a liquid (water) hold-out of greater than about 0.9 psi, preferably greater than about 0.9 psi and less than about 6.0 psi, may minimize pouch ballooning while still preventing ostomy effluent leakage.

In an embodiment, the filter assembly 116 may comprise the backing layer 102 formed from a LDPE film having a thickness of about 5 mil, the filter media 118 formed from an activated carbon reticulated PU foam having a net density of about 26 $kg/m^3$ to about 30 $kg/m^3$ (tested according to ISO 845), and the membrane layer 104 formed from a SMS PP nonwoven having a basis weight of about 44 gsm, wherein the filter assembly 116 may be covering the outlet opening 106 having an area of about 0.06 $inch^2$ to about 0.07 $inch^2$ and configured to have an airflow rate @0.18 psi of greater than about 10 cc/s and less than about 40 cc/s and a liquid (water) hold-out of greater than about 0.9 psi and less than about 3.0 psi. In an embodiment, the filter assembly 116 may be configured to cover the outlet opening 106 having an area of about 0.0625 $inch^2$ and have an airflow rate @0.18 psi of greater than about 15 cc/s and less than about 35 cc/s and a liquid (water) hold-out of greater than about 1.0 psi and less than about 2.0 psi. The filter assembly 116 may be provided in various shapes, for example, circular, elliptical, rectangular, or square shapes.

Figure 7:
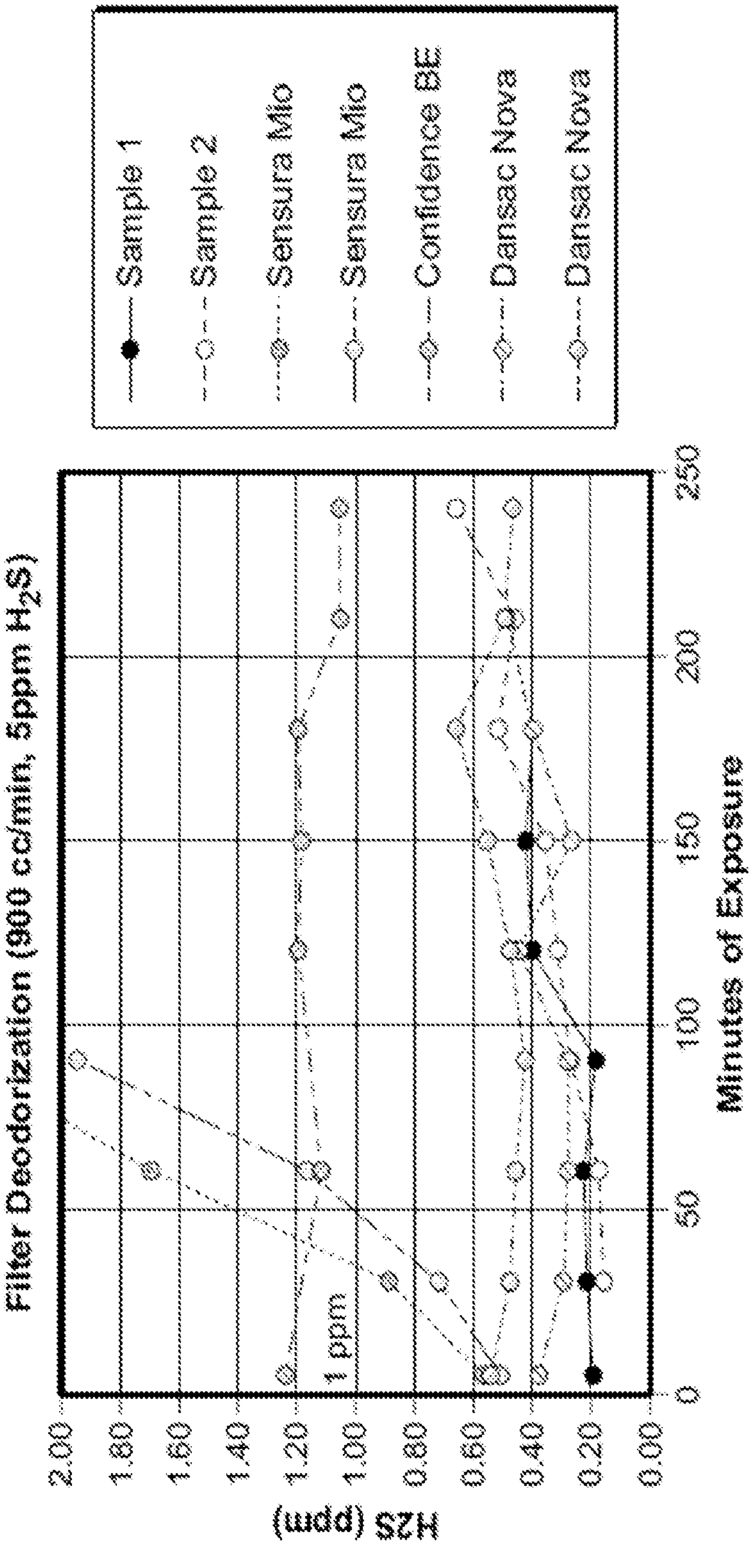
FIG. 7 is a graph of volatile analysis test results using $H_2S$ challenge gas.
Figure 8:
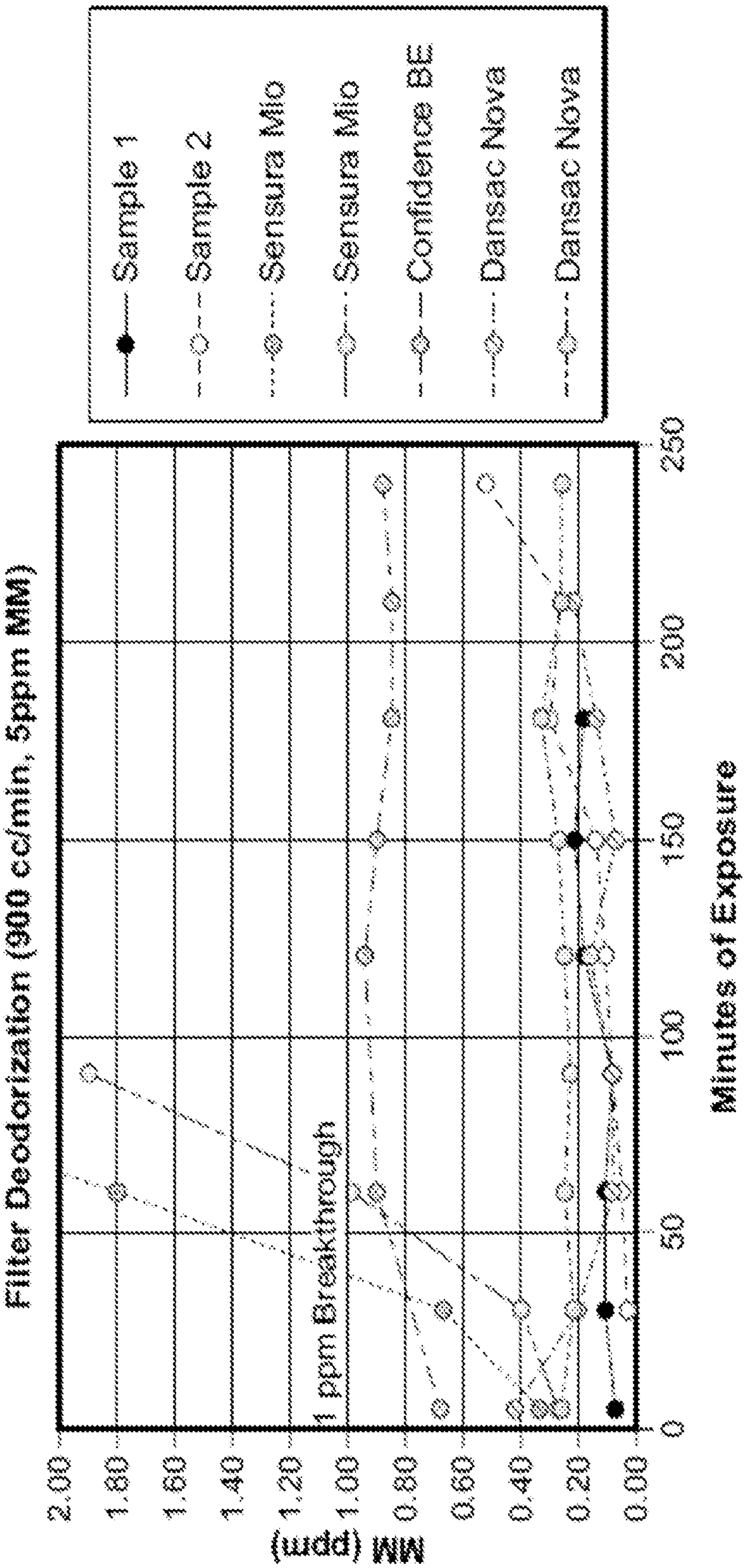
FIG. 8 is a graph of volatile analysis test results using methyl mercaptan challenge gas.

Samples of the filter assembly 116 having a square-shaped body with the side length of 1.165 inches and comprising the backing layer 102 formed from a LDPE film having a thickness of about 5 mil, the filter media 118 formed from an activated carbon reticulated PU foam having a net density of about 26 $kg/m^3$ to about 30 $kg/m^3$ (tested according to ISO 845), and the membrane layer 104 formed from a SMS PP nonwoven having a basis weight of about 44 gsm were prepared and tested for deodorization properties along with prior art filter assemblies. Volatile analyses using a challenge gas containing 5 ppm $H_2S$ in dry nitrogen and a challenge gas containing 5 ppm methyl mercaptan (MM) in dry nitrogen were conducted. The test parameters included: challenge gas humidified to 25% RH (relative humidity), a flow rate of challenge gas to filter of 15 cc/s, and a back pressure of 0.8 psi. FIG. 7 is a graph of volatile analysis test results using the $H_2S$ challenge gas, and FIG. 8 is a graph of volatile analysis test results using the MM challenge gas. As shown in FIGS. 7 and 8, the filter assembly 116 (referred to as "Sample 1" and "Sample 2") exhibited better deodorization properties when compared to Coloplast SenSura® Mio filter assembly samples including an e-PTFE membrane and Salts Healthcare Confidence BE® filter assembly samples including an e-PTFE membrane, and exhibited similar deodorization properties when compared to Dansac NovaLife filter assembly samples including a UHMW PE membrane.

Referring back to FIG. 1, the multi-stage filter protection 117 may comprise a prefilter 124 arranged to cover the gas outlet opening 106 and sealed to an inner surface of the pouch wall 112 and a protective panel 120 covering the prefilter 124 and sealed to an inner surface of the pouch wall 112. In such an embodiment, the protective panel 120 may function as a coarse prefilter and a first line of protection and the prefilter 124 may function as a fine prefilter and a second line of protection to provide a multiple protection for the filter assembly 116 from ostomy effluent collected in the pouch.

In an embodiment, the prefilter 124 may comprise a first layer 125 and an optional second layer 123. The first layer 125 may be configured for fine particulate blocking and formed from any suitable material comprising sufficient gas flow path/channels to provide a substantially lower gas flow resistance when compared to the optional second layer 123 or the membrane layer 104. Suitable materials for the first layer 125 may include, but are not limited to, open-cell foams and reticulated foams including about 10 pores per inch (ppi) about 250 ppi, preferably about 30 ppi to about 200 ppi. For example, the first layer 125 may be formed a reticulated foam including about 200 ppi. Suitable materials for the first layer 125 are not limited to foam materials and may include other similar materials configured for fine particular blocking and a relatively low gas flow resistance.

The first layer 125 may have a thickness of about 1/32 inches to about ½ inches, preferably about 1/16 inches to about ¼ inches, and more preferably about ⅛ inches. In an embodiment, the first layer 125 may be formed from, a reticulated PU foam having about 45 ppi and a thickness of about 1/32 inches. In some embodiment, the first layer 125 may be laminated to the second layer 123.

The second layer 123 may be formed from a suitable material configured to provide some support for the first layer 125 during handling and processing and heat sealability to the pouch wall 112. Suitable materials for the second layer 123 include, but are not limited to, nonwoven materials, membrane materials, gas permeable polymeric materials and the like. For example, the second layer 123 may be formed from a polyester (PET) nonwoven or a SMS PP nonwoven having a basis weight of about 10 gsm to about 500 gsm, preferably about 20 gsm to about 100 gsm, and more preferably about 30 gsm to about 50 gsm. The prefilter 124 may be configured such that a user may apply pressure through the pouch walls to squeeze out any liquid absorbed by the first layer 125. The second layer 123 is optional. In embodiments where the prefilter 124 does not include the second layer 123, the first layer 125 may be directly sealed to the pouch wall 112.

The protective panel 120 may be formed from a suitable microperforated film and sealed to the pouch wall 112 via a peripheral seal. In an embodiment, the protective panel 120 may be configured and sized slightly larger than the prefilter 123 to cover and seal around the prefilter 123. In other embodiments, the protective panel may be configured to cover about ⅕ to about ⅔ of an upper portion of the ostomy pouch, preferably, about ¼ to about ½ of an upper portion of the ostomy pouch. The microperforated film may be formed from a suitable polymeric material configured for heat sealing to the pouch wall 112. In an embodiment, the protective panel 120 may be formed from a copolymer comprising about 8% ethylene-vinyl acetate (EVA). The protective panel 120 may have a thickness of about 0.5 mil to about 10 mil, preferably about 1 mil to about 5 mil.

The protective panel 120 may comprise microperforations in a portion, in more than one portion or throughout the whole area of the protective panel 120. In the embodiment of FIG. 1, the protective panel 120 may include microperforations 130 only in a lower portion of the protective panel 120. In such an embodiment, gas collected in the ostomy pouch 100 may flow through the microperforations 130 in the lower portion of the protective panel 120 and flow upward through the prefilter 124 and exit the pouch through the gas outlet opening 106 and flow through the membrane layer 104 and filtered via the filter media 118 before exiting the filter assembly 116 as shown by the arrows in FIG. 1.

The protective panel 120 may include microperforations defined by a plurality of generally circular cylindrical openings having a diameter of about 50 μm to about 500 μm, preferably about 100 μm to about 450 μm, more preferably about 150 μm to about 400 μm. In an embodiment, the protective panel 120 may include microperforations in a lower portion of the protective panel 120, wherein the microperforations have a pore-density of about 10 pores per inch (ppi) to about 500 ppi, preferably about 100 ppi to about 300 ppi. In some embodiments, the protective panel 120 may include microperforations of various sizes, various patterns, various shapes, and/or in selected portions of the protective panel 120.

Figure 9:
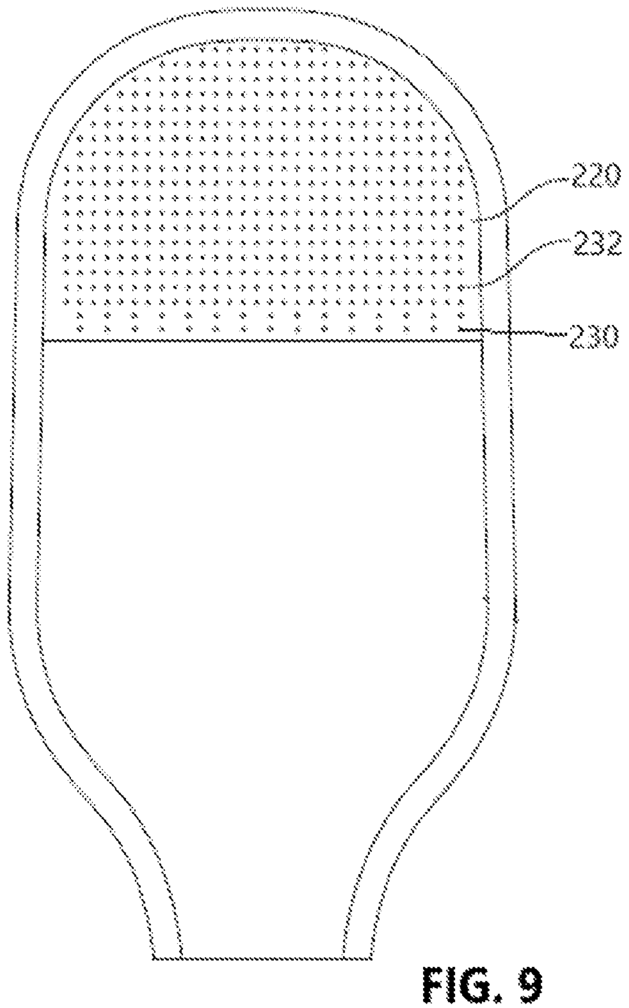
FIG. 9 is a schematic perspective view of an ostomy pouch including a protective panel formed from a perforated film according to an embodiment.

FIG. 9 shows an ostomy pouch comprising a protective panel 220 according to an embodiment, wherein the protective panel 220 includes a first set of microperforations 230 in a lower portion of the protective panel 220 and a second set of microperforations 232 arranged above the first set of microperforations 230. The first set of microperforations 230 may be defined by a plurality of openings having a larger diameter than those of the second set of microperforations 232. For example, the first set of microperforations 230 may be defined by a plurality of generally circular cylindrical openings having a diameter of about 250 μm to about 500 μm, preferably about 300 μm to about 400 μm, and more preferably about 350 μm to about 380 μm. The second set of microperforations 232 may be defined by generally circular cylindrical openings having a diameter of about 50 μm to about 300 μm, preferably about 100 μm to about 250 μm, and more preferably about 125 μm to about 175 μm.

In an embodiment, the protective panel 220 may be formed from a copolymer film containing about 8% EVA and having a thickness of about 2.1 mil and may comprise microperforations, wherein the microperforations include the first set of microperforations 230 defined by a plurality of openings having a diameter of about 380 μm arranged in two rows and the second set of microperforations 232 defined by a plurality of opening having a diameter of about 150 μm arranged in 24 rows, wherein the microperforations have a pore-density of about 100 ppi. The protective panel 220 may be configured for coarse particulate blocking and heat seal to pouch walls along its periphery. In some embodiments, the protective panel 220 may be provided with slits or openings proximate a lower periphery to allow any liquid accumulated between the protective panel and the pouch wall to flow down.

Figure 10:
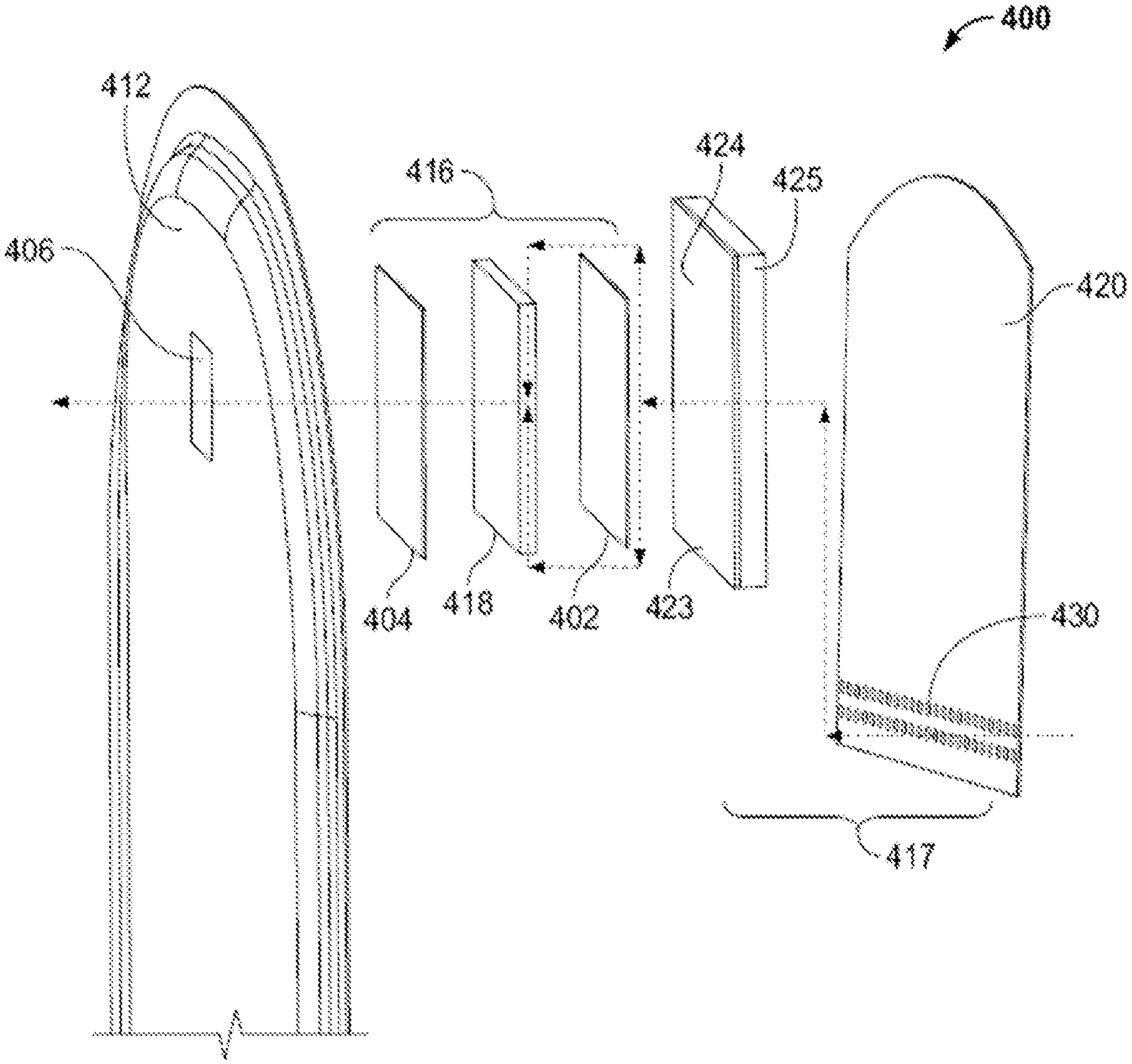
FIG. 10 is a partial exploded view of an ostomy pouch comprising a filter assembly according to another embodiment.

FIG. 10 is a partial exploded view of an ostomy pouch 400 according to an embodiment. The ostomy pouch 400 may be configured similar to the ostomy pouch 100 comprising a filter assembly 416 and an optional multi-stage protection 417, which may include a protective panel 420 and a prefilter 424. In the embodiment of FIG. 10, the filter assembly 416 may be attached to an inner surface of a distal pouch wall 412. The filter assembly 416 may comprise a backing layer 402, a filter media 418, and a membrane layer 404. The filter assembly 416 may be arranged to cover a gas outlet opening 406 defined in the pouch wall 412 and attached to the pouch wall 412, such that the membrane layer 404 may be arranged adjacent the gas outlet opening 406. In this embodiment, the filter assembly 416 and the multi-stage protection 417 may be configured and arranged to allow the gas collected in the collection area to flow through microperforations 430 of the protective panel 420, and flow through the prefilter 424, then flow around the backing layer 402, and radially flow through the filter media 418, and flow through the membrane layer 404 before exiting the ostomy pouch 400 through the outlet opening 406.

It is understood that the relative directions described above, e.g., "upward," "downward," "upper," "lower," "above," "below," are used for illustrative purposes only and may change depending on an orientation of the ostomy pouch and/or the patient. Accordingly, this terminology is non-limiting in nature. In addition, it is understood that one or more various features of an embodiment above may be used in, combined with, or replace other features of a different embodiment described herein.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy pouch comprising:

a body-side wall and a distal-side wall joined at an outer periphery and defining an interior volume comprising a collection area;

an inlet for receiving ostomy effluent;

an outlet for egress of gas collected in the collection area; and a filter assembly covering the outlet, the filter assembly comprising a backing layer, a filter media, and a membrane layer formed from a spunbond-meltblown-spunbond polypropylene (SMS PP) nonwoven, wherein the backing layer has a lower gas permeability than the filter media;

wherein the ostomy pouch is configured to have an airflow rate @ 0.18 psi of greater than about 10 cc/s and less than about 40 cc/s and a liquid (water) hold-out of greater than about 0.9 psi and less than about 6.0 psi.

2. The ostomy pouch of claim 1, wherein the filter media is formed from an activated carbon impregnated foam, wherein the activated carbon impregnated foam is hydrophobic.

3. The ostomy pouch of claim 2, wherein the filter media is formed from an activated carbon impregnated reticulated polyurethane (PU) foam.

4. The ostomy pouch of claim 1, wherein the backing layer is formed from a low density polyethylene film, the filter media is formed from an activated carbon reticulated PU foam having a net density of about 26 $kg/m^3$ to about 30 $kg/m^3$ (tested according to ISO 845), and the membrane layer is formed from a SMS PP nonwoven having a basis weight of about 44 gsm, wherein the outlet is defined by an opening having an area of about 0.06 $inch^2$ to about 0.07 $inch^2$, wherein the ostomy pouch is configured to have a liquid (water) hold-out of greater than about 0.9 psi and less than about 3.0 psi.

5. The ostomy pouch of claim 1, wherein the backing layer is formed from a low density polyethylene film, the filter media is formed from an activated carbon reticulated PU foam having a net density of about 26 $kg/m^3$ to about 30 $kg/m^3$ (tested according to ISO 845), and the membrane layer is formed from a SMS PP nonwoven having a basis weight of about 44 gsm, wherein the outlet is defined by an opening having an area of about 0.0625 $inch^2$, and wherein the ostomy pouch is configured to have an airflow rate @0.18 psi of greater than about 15 cc/s and less than about 35 cc/s and a liquid (water) hold-out of greater than about 1.0 psi and less than about 2.0 psi.

6. The ostomy pouch of claim 1, wherein the filter assembly is attached to an outer surface of one of the body-side wall and the distal-side wall.

7. The ostomy pouch of claim 6, wherein the filter assembly is configured to provide a radial gas flow path through the filter media, wherein the filter assembly is configured to direct the gas egressing through the outlet to flow through the membrane layer and radially flow through the filter media and exit the filter assembly through at least one gas outlet provided proximate an outer periphery of the filter assembly.

8. The ostomy pouch of claim 1, wherein the filter assembly is attached to an inner surface of one of the body-side wall and the distal-side wall.

9. The ostomy pouch of claim 8, wherein the filter assembly is configured to provide a radial gas flow path through the filter media, wherein the filter assembly is configured to allow the gas collected in the collection area to flow into the filter assembly through at least one gas inlet provided proximate an outer periphery of the filter assembly and radially flow through the filter media and flow through the membrane layer before exiting the ostomy pouch through the outlet.

10. An ostomy pouch comprising:

a body-side wall and a distal-side wall joined at an outer periphery and defining an interior volume comprising a collection area;

an inlet for receiving ostomy effluent;

an outlet for egress of gas collected in the collection area; and a filter assembly covering the outlet, wherein the ostomy pouch is configured to have an airflow rate @ 0.18 psi of greater than about 10 cc/s and less than about 40 cc/s and a liquid (water) hold-out of greater than about 0.9 psi and less than about 6.0 psi, wherein the outlet is defined by an opening having an area of about 0.06 $inch^2$ to about 0.07 $inch^2$.

11. An ostomy pouch comprising:

a body-side wall and a distal-side wall joined at an outer periphery and defining an interior volume comprising a collection area;

an inlet for receiving ostomy effluent;

an outlet for egress of gas collected in the collection area;

a filter assembly covering the outlet;

a prefilter; and a protective panel, wherein the prefilter and the protective panel are configured to protect the filter assembly from ostomy effluent, wherein the filter assembly is attached to an outer surface of the distal-side wall or an inner surface of the distal-side wall, and the prefilter and the protective panel are attached to an inner surface of the distal-side wall, wherein the ostomy pouch is configured to have an airflow rate @ 0.18 psi of greater than about 10 cc/s and less than about 40 cc/s and a liquid (water) hold-out of greater than about 0.9 psi and less than about 6.0 psi.

12. The ostomy pouch of claim 11, wherein the ostomy pouch is configured to provide a flow path for the gas collected in the collection area to flow through microperforations provided in the protective panel and flow through the prefilter and exit the ostomy pouch through the outlet and flow through the membrane layer and flow through the filter media radially before exiting the filter assembly.

13. The ostomy pouch of claim 11, wherein the ostomy pouch is configured to provide a flow path for the gas collected in the collection area to flow through microperforations provided in the protective panel and flow through the prefilter and enter the filter assembly through at least one gas inlet provided proximate an outer periphery of the filter assembly and radially flow through the filter media and flow through the membrane layer before exiting the ostomy pouch through the outlet.

* * * * *